(12) United States Patent  (10) Patent No.: US 7,418,081 B2
Holler et al.  (45) Date of Patent: Aug. 26, 2008

(54) MEDICAL IMAGING EQUIPMENT

(75) Inventors: Wolfgang Holler, Erlangen (DE);
Gregor Niewalda, Erlangen (DE);
Martin Ramsauer, Pyrbaum (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/632,140

(22) PCT Filed: Jul. 11, 2005

(86) PCT No.: PCT/EP2005/053312

§ 371 (c)(1),
(2), (4) Date: Jan. 10, 2007

(87) PCT Pub. No.: WO2006/005744

PCT Pub. Date: Jan. 19, 2006

(65) Prior Publication Data

US 2007/0189447 A1    Aug. 16, 2007

(30) Foreign Application Priority Data

Jul. 15, 2004   (DE) ....................... 10 2004 034 239

(51) Int. Cl.
*H05G 1/64* (2006.01)
*A61B 6/04* (2006.01)

(52) U.S. Cl. ........................................ 378/98.8; 378/37

(58) Field of Classification Search ............... 378/4, 378/19, 37, 51, 54, 98.8, 95, 108, 195
See application file for complete search history.

(56) References Cited

U.S. PATENT DOCUMENTS

| 4,104,529 | A | * | 8/1978 | Gaudel ....................... 378/172 |
| 5,148,460 | A | * | 9/1992 | Aichinger ................... 378/108 |
| 5,170,419 | A | | 12/1992 | Johansson et al. |
| 5,210,416 | A | * | 5/1993 | Seto et al. .................. 250/589 |
| 5,386,447 | A | * | 1/1995 | Siczek .......................... 378/37 |
| 6,304,627 | B1 | | 10/2001 | Horbaschek |

FOREIGN PATENT DOCUMENTS

DE  33 19 622 A1  12/1984

* cited by examiner

*Primary Examiner*—Irakli Kiknadze
(74) *Attorney, Agent, or Firm*—Brinks, Hofer, Gilson & Lione

(57) ABSTRACT

A medical imaging equipment is described, including a radiation source for emitting measuring radiation, a receiver for receiving the measuring radiation, and a measuring region in which an object to be measured is placed, and which is situated in the beam path of the measuring radiation The receiver comprises a support which can be pivoted about a rotational axis and is adapted to mount at least two receiving devices. The receiving surfaces may be disposed alternately into a measuring position. A surface of the receiving device is parallel to the rotational axis of the support, and the rotational axis of the support is substantially perpendicular to the beam path of the measuring radiation.

23 Claims, 6 Drawing Sheets

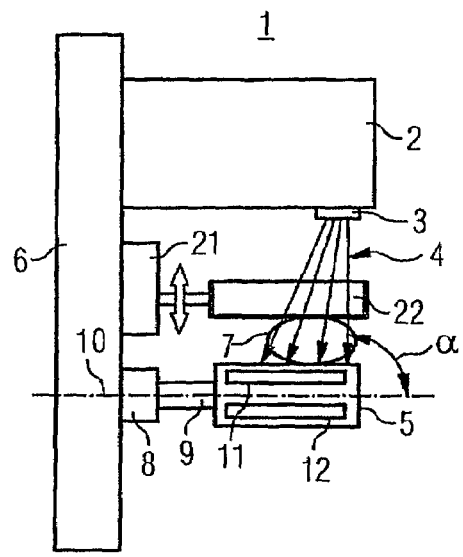
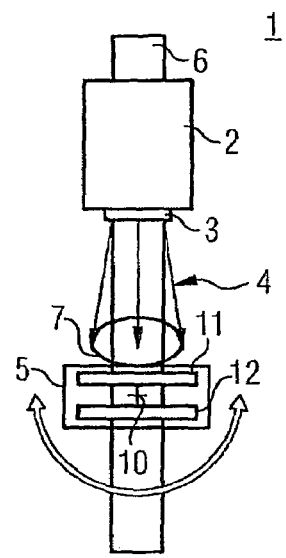
FIG 1A FIG 1B
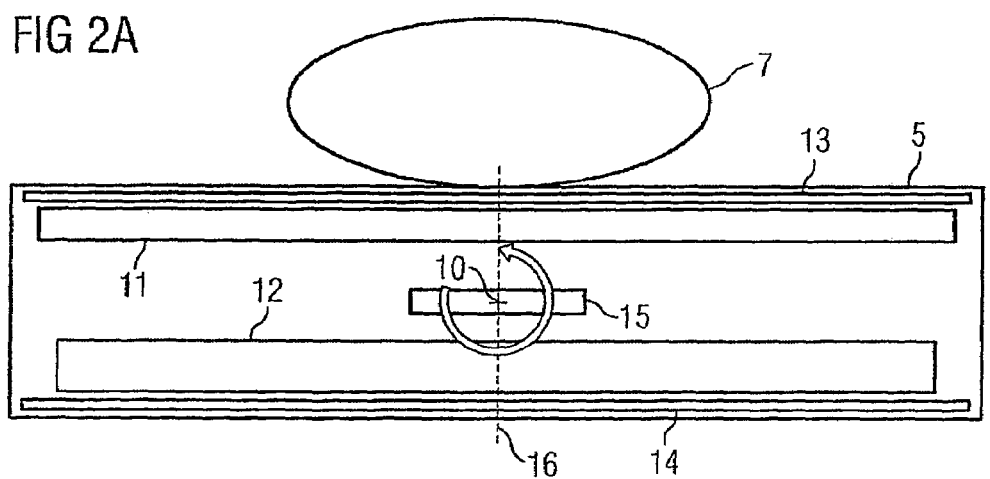
FIG 2A

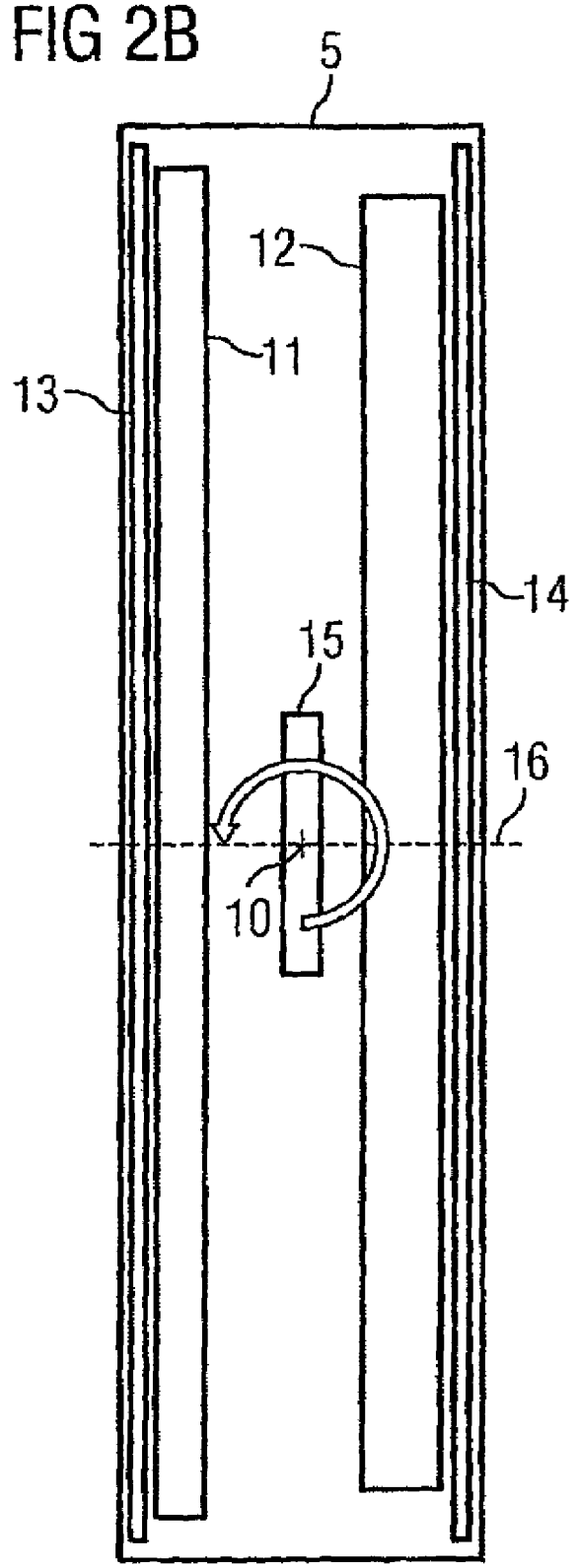

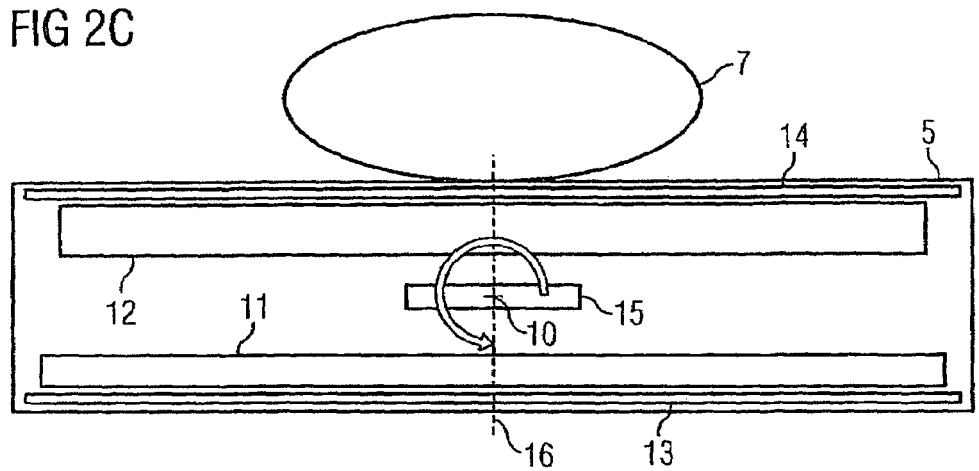
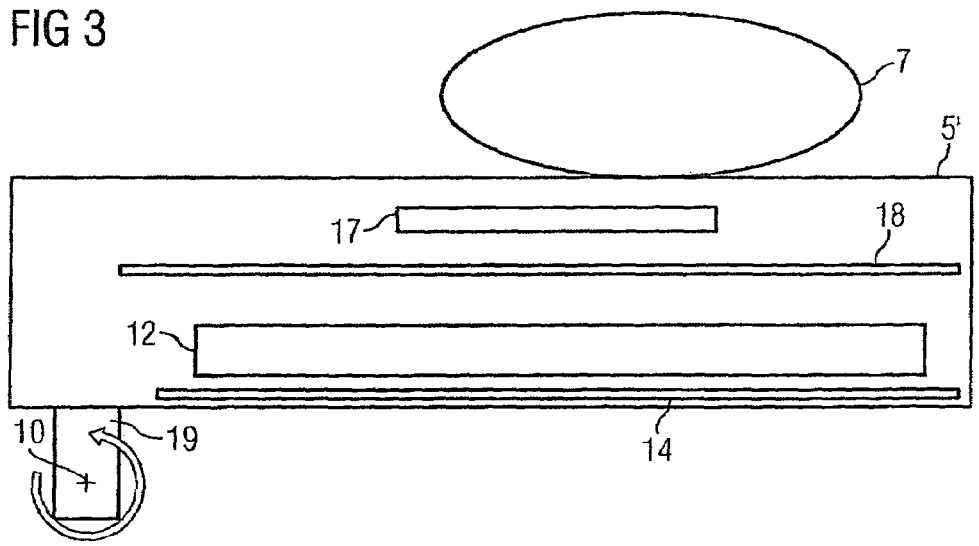

MEDICAL IMAGING EQUIPMENT

RELATED APPLICATIONS

The present patent document is a continuation of PCT Application Serial No. PCT/EP2005/0533312, filed Jul. 11, 2005, designating the United States, which claims priority to German patent application No. 10 2004 034 239.3, filed on Jul. 15, 2004, both of is the applications hereby incorporated by reference.

TECHNICAL FIELD

The present application relates to medical imaging equipment for obtaining mammographic images, and in particular to imaging on several recording media.

BACKGROUND

Mammography is an x-ray examination of the female breast carried out using medical imaging equipment to obtain mammographic images. Such devices generally have a radiation source for x-rays. The female breast that is to be examined is x-rayed and a radiographic (fluoroscopic) image is obtained on an x-ray film arranged in the beam path below the female breast. During the examination, the female breast is normally held between a compression plate and an object table.

The use of x-ray films has the advantage that it represents a solution that is technically relatively sophisticated and at least in its purchase price relatively inexpensive and at the same time allows the radiographic image obtained by the x-ray film to be archived permanently.

A further advantage of using x-ray films is that x-ray films have a very large receiving surface, typically 18×24 cm or 24×30 cm, and a relatively high spatial resolution of about 14 Lp/mm (Lp=line pairs), which allows a high-definition full x-ray photo of the female breast to be made in a single measurement.

Instead of the x-ray film, which can only be used once, the use of a charge-coupled-device (CCD) sensor is known. The CCD sensors can be used in mammography equipment in the place of the x-ray film.

CCD sensors are electronic components which are suitable for spatial resolution measurement of radiation, in particular, of x-rays and, as a rule, are a matrix of radiation-sensitive cells, also known as pixels. To ensure easy adaptation to existing equipment, the CCD sensor is frequently integrated into a holder in the form of a conventional x-ray film cassette. The advantage of using CCD sensors is that currently available CCD sensors have a resolution of between 10 and 20 Lp per millimeter, which exceeds the resolution of x-ray films and the images are made available immediately and can be processed digitally. Thus, CCD sensors (unlike x-ray films) are suitable for obtaining real-time images (for example, of a biopsy).

The disadvantage of using CCD sensors is that, at present, CCD sensors with the required high resolution have a receiving surface which is markedly smaller than the receiving surface of x-ray films. Therefore, high resolution CCD sensors are currently only suitable for detailed x-ray photos of the female breast.

In addition, within the scope of FFDM (Full-Field Digital Mammography) the use of low resolution digital detectors is known.

The digital detectors used for FFDM currently have a typical resolution of 5 to 10 Lp per millimeter and, hence, a lower resolution than x-ray films. However, it is possible to realize receiving surfaces whose size is similar to the size of the receiving surfaces of conventional x-ray films. Therefore, using FFDM detectors, it is possible to produce a complete image of the female breast in one recording.

Thus, an advantage of the FFDM detectors is that the images are available in real time, the images can be digitally processed, and the receiving surfaces are relatively large. The current disadvantage is the relatively low resolution.

In an alternative to FFDM detectors, the use of digital luminescence radiography with storage screen technology to obtain mammographic images is also known. The resolution that can be achieved using this technology is currently about 8 Lp/mm.

In order to be able to combine the advantages, for example, of an FFDM detector with the advantage of an x-ray film, medical imaging equipment for obtaining mammographic images is known, which equipment has two receiving surfaces for x-rays.

A related art device with two receiving surfaces is shown in FIG. 6. The medical imaging equipment 61 for obtaining mammographic images has a head 62 with a radiation source 63 for emitting x-rays 64 and a receiving device 65.

Both the head 62 and the receiving device are supported by a support column 66, which is attached to a floor stand or to the ceiling of a room.

In the device shown in FIG. 6, the receiving device 65 has a first receiving surface 71 in the form of a holder for x-ray films and a second receiving surface 72 in the form of a large-area low-resolution detector for FFDM recordings.

The two receiving surfaces 71 and 72 are arranged at right angles to each other and are supported by a support 65 of the receiving device via a mounting 68 attached to the support column 66. The two receiving surfaces 71 and 72 can be pivoted around a rotational axis 70 alternately into a measuring position by turning the support manually. The rotational axis makes an angle of essentially 45° to the beam path of the x-rays 64 emitted by the radiation source 63.

The 45° angle between the rotational axis 70 and the beam path of the x-rays 64, together with the receiving surfaces 71, 72, which are arranged at an angle of 90° with respect to each other, ensures that after the support 65 has been pivoted about the rotational axis 70, one of the receiving surfaces 71 is disposed outside the beam path parallel to the beam path and the other receiving surface 72 is disposed inside the beam path at right angles to the beam path of the x-rays 64.

Provision is made for a measuring region, which is situated in the beam path between a respective receiving surface 71 or 72 in the measuring position and the radiation source 64, the measuring region being provided to arrange an object 67 for measurement.

In addition, a compression plate 75 which is transparent to the measuring radiation is provided in the beam path above the object for measurement 67.

The compression plate 75 is supported by a compression device 74. A vertical movement of the compression plate 75 effected by the compression device 74 enables the object for measurement 67 to be compressed between the compression plate 75 and a supporting surface formed by the respective receiving surface 71 or 72.

The previously known equipment has a disadvantage that it has a high space requirement 73 because of the wide pivoting movement about the axis 70 of the receiving surfaces 71 and 72 held by the support 65.

In addition, the manufacture of a correspondingly pivotable mechanical connection with the respective receiving surfaces 71, 72 having the precision required in the medical sector is technically very complex, and hence expensive.

SUMMARY

Medical imaging equipment is described comprising a radiation source for emitting measuring radiation, a receiving device for receiving the measuring radiation, and a measuring region, in which an object for measurement is placed and which is situated in the beam path of the measuring radiation between the radiation source and the receiving device. The receiving device has a support which may be pivoted about a rotational axis, the support supporting at least two receiving devices for the measuring the radiation and moves the receiving devices alternately into a measuring position. The receiving devices are arranged parallel to the rotational axis of the support, and the rotational axis of the support is approximately at right angles to the beam path of the measuring radiation.

The receiving devices are disposed substantially parallel to the rotational axis of the support, and the rotational axis of the support is substantially at right angles to the beam path of the measuring radiation. Rotating the support results in a movement that, in a horizontal direction, does not take up any more space than the support surfaces when the support is in the measuring position. The support may be designed as a shared housing for the receiving devices. Thus, the equipment has a space-efficient construction. In addition, it is possible to provide a particularly simple and robust mechanical connection of the support to the equipment.

The rotational axis of the support and the beam path of the measuring radiation make an angle of between 80° and 100°, particularly between 85° and 95°, preferably between 88° and 92° and more preferably of 90°.

The rotational axis may be arranged between the receiving surfaces and the receiving devices may be disposed so that each is approximately bisected by a perpendicular projection of the rotational axis.

After the support has been turned, the respective receiving device comes to rest in the respective measuring position centric to the rotational axis. This allows the equipment to be operated intuitively and, therefore, easily. In addition, in this way, errors caused by an erroneous estimation of the spatial position of the receiving surface may be avoided. In addition, when being pivoted, the protrusion of the support is reduced.

Generally, the rotational axis is arranged centrally in the beam path of the measuring radiation and may be situated in the geometric center of a volume enclosed by the support for the receiving devices.

In an aspect where the rotational axis is in the geometric center of a volume enclosed by the support, the support has a small orbit when it pivots. Further, a user can intuitively predict the course of a pivoting movement about the rotational axis.

The support may also have a surface for placing the object for measurement. The upper surface of the support can be used as the lower compression surface for the compression of the female breast while a mammography recording is being carried out. This reduces the number of components required and, hence, the cost of the equipment.

A control device may be situated between the receiving devices and carried by the support, for controlling the received measuring radiation. By using a control device carried by the support for controlling the received measuring radiation, it is possible to use a shared control device for different receiving devices, which reduces the number of components required. The control device can, for example, be used for an automatic exposure speed control.

The support may carry a shield, which is arranged in the beam path of the measuring radiation and disposed between the radiation source and the receiving devices, which are not in the measuring position.

By shielding the receiving devices not in the measuring position, it is possible to prevent x-rays from emerging from a side of the support away from the radiation source so that parts of the patient's body that are not the subject of the examination from being radiated. In this way the patient's exposure to radiation can be reduced. Moreover, the shield may also prevent unintentional exposure of the receiving surface that is not situated in the measuring position and also may prevent this receiving surface being exposed to radiation.

In an aspect, the support carries two essentially parallel receiving devices for the measuring radiation. A construction of this type can be realized using a compact design.

In another aspect, the support carries three receiving devices for the measuring radiation, wherein adjacent receiving devices together are disposed at an angle of essentially 60° with respect to each other. This allows three receiving surfaces to be realized in one compact design.

In yet another aspect, the support carries four receiving devices for the measuring radiation, wherein adjacent receiving surfaces together are disposed at an angle of essentially 90° with respect to each other. This construction allows the use of four receiving surfaces while at the same time retaining a compact design.

The measuring radiation emitted by the radiation source is an x-ray beam. One of the receiving devices is a solid state detector for x-rays, and another of the receiving devices is an x-ray film. One of the receiving devices may be a luminescence radiography screen. Screens of this kind are also known as "storage screens".

BRIEF DESCRIPTION OF THE DRAWINGS

FIG. 1A shows a schematic side view of medical imaging equipment for obtaining mammographic images in accordance with a first example;

FIG. 1B shows a schematic front view of the medical imaging equipment of FIG. 1A;

FIGS. 2A, 2B, 2C show schematic sectional views through a support and receiving devices, where the different views show different states of pivoting;

FIG. 3 shows a schematic sectional view through an alternative example of support arrangements of the receiving devices of FIG. 2;

DETAILED DESCRIPTION

Figure 4:
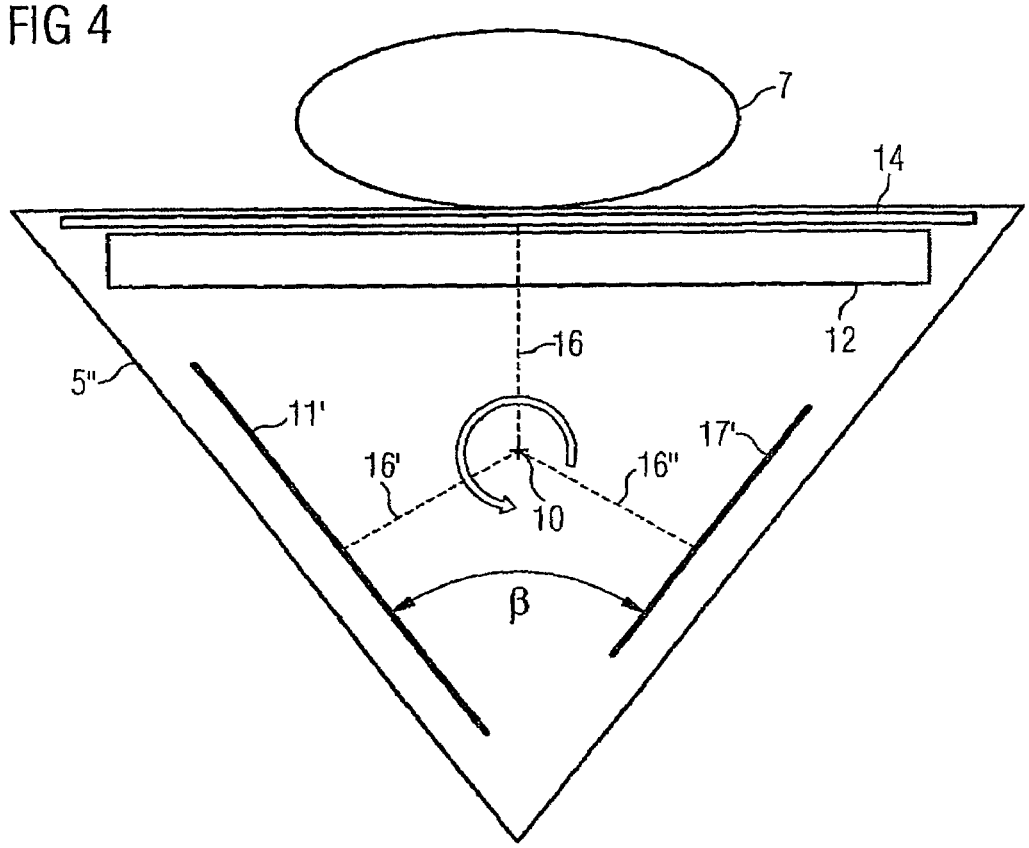
FIG. 4 shows a schematic sectional view through a support of and receiving devices of a second example.

In the following, the examples are described in detail with reference to the attached drawings. In the drawings, identical reference signs mark identical components or components with the same functions in the various views, FIG. 1A shows a side view and FIG. 1B a front view of the equipment. The medical imaging device 1 has a radiation source 3 for emitting x-rays 4, carried by a head 2. The head 2 is carried by a support column 6. Underneath the radiation source 3, there are receiving devices for receiving the x-rays 4 emitted by the radiation source 3.

The receiving devices are carried by the support column 6 and may include a motor 8, a first bracket 9 carried by motor 8 and a support 5 carried by the first bracket 9. The support 5, which may be made out of a carbon fiber material, is situated in the beam path of the measuring radiation 4.

Alternatively, the support 5 can be made from a different material, such as, for example, plastic. Such materials are selected to be substantially transparent to the measuring radiation.

A measuring region for arranging an object for measurement 7 is provided between the support 5 and the radiation source 3, in the radiation path of the x-rays 4, and the object for measurement may be a female breast.

As can be seen from the FIGS. 1A and 1B, an upper surface of the support 5 turned towards the radiation source 3, is also used as a contact surface for the respective object for measurement (here, the female breast 7).

A compression plate 22 which is substantially transparent to the respective measuring radiation is provided in the beam path of the x-rays 4 above the object for measurement 7. The compression plate 22 may be made from a plastic material or materials as used for the support 5.

The compression plate 22 is carried by a compression device 21, which is attached to the support column 6 of the medical imaging device 1. The compression plate 22 may be moved vertically by the compression device 21, and the object for measurement 7 may be compressed between the compression plate 22 and the contact surface formed by the support 5. The surface of the support 5 may thus also used as the lower compression surface. For improved clarity of presentation, the compression plate 22 and the compression device 21 are not shown in FIG. 1B.

The support 5 may be pivoted about a rotational axis 10 by the motor 8 via the first bracket 9. Thereby, the rotational axis 10 is disposed at an angle α of approximately 90° to the beam path of the x-rays 4. The angle α may be between 80° and 100°, particularly between 85° and 95° and preferably between 88° and 92°.

According to an alternative aspect, the support 5 may be pivoted pivoted about the rotational axis 10 manually.

As can be seen from the FIGS. 1A and 1B, the rotational axis 10, according to the first embodiment of this invention, is in line with the measuring region, arranged centrally in the beam path of the x-rays 4.

The support 5 carries a first receiving device 11 for the x-rays 4 as well as a second receiving device 12 for the x-rays 4. In this example, the first receiving device 11 may be a removable x-ray film cassette having an x-ray film with a recording surface of, for example, 18×24 cm or 24×30 cm and the second receiving device 12 may be a large-surface low-resolution solid-state detector for x-rays for producing FFDM (full field digital mammography) images.

As an alternative to the x-ray film cassette with an x-ray film, a CCD sensor incorporated into an x-ray film cassette may be used. The recording surface of a CCD sensor of this kind is, at present smaller than that of an x-ray film.

As the FIGS. 1A and 1B show, the receiving devices 11 and 12 are arranged essentially parallel to each other and parallel to the rotational axis 10 of the support 5. In this example, the rotational axis 10 is arranged between the receiving devices 11 and 12. By pivoting the support 5 180° clockwise or anticlockwise about the rotational axis 10, the first or the second receiving device 11, 12 can be moved, alternately, into a measuring position.

In the measuring position, the respective receiving device 11 or 12 adjacent to the measuring region is arranged in the beam path for the x-rays 4 in such a way that a surface thereof is aligned towards the radiation source 3. Furthermore, the beam path of the x-rays 4 and a surface of the receiving device 11 or 12 located in the measuring position are oriented at an angle of substantially 90°.

Thus, by pivoting the support 5, the first or the second receiving surface 11 or 12 alternately come to rest on the upper side of the support 5. In FIGS. 1A and 1B, the fixing of the support 5 and, thus, the fixing of the respective receiving device 11 and 12 in the respective measuring position is achieved via the motor 8. However, alternatively, a separate fixing device can be provided, which device preferably has shielding.

In FIGS. 2A, 2B and 2C the support 5 of the medical imaging equipment 1 shown in FIGS. 1A and 1B is represented in different pivot positions. These are schematic sectional views through the support 5 at right angles to the rotational axis 10.

The support 5 carries a first receiving device 11 which may be an exchangeable x-ray film cassette, which can contain an x-ray film or a CCD sensor. In addition, the support 5 carries a second receiving device 12 which is a low resolution digital sensor for FFDM recordings.

A first or a second filter 13, 14 is arranged in front of the x-ray film cassette 11 or in front of the low-resolution digital sensor 12. In this example, the filters 13 and 14 are scattered radiation grids, which are each adapted to the receiving device adjacent x-ray sensor.

The support 5, shown in FIGS. 2A to 2C, may carry a control device 15, which is used for the automatic control of the received x-rays 4. The control device 15 may be shared by the two receiving devices 11 and 12. By using a shared control device 15, the number of components used can be kept low. This enables the production costs to be reduced.

When an x-ray film is used in the receiving device 11, it the control device 15 may assume the function of an automatic exposure control (AEC) detector. Thus, the control device measures the radiation received in order to calculate the correct or optimal exposure time for the x-ray film.

When a CCD sensor is used in the receiving device 11 or when the low resolution digital sensor 12 is used, the correct or optimal exposure time is automatically determined by the respective sensor. An additional AEC detector is not required. However, the control device 15 can be used as an additional safety device, so as to avoid unnecessary exposure to radiation if the CCD sensor or the low resolution digital sensor 12 fails.

As shown in FIGS. 2A to 2C, the support 5 carries the receiving devices 11 and 12, together with the associated filters 13 and 14. The rotational axis 10 is arranged such that a perpendicular projection 16 of the rotational axis 10 onto the receiving surface 11 or 12, bisects the surface of the receiving device 11 or 12, respectively. The perpendicular projection 16 is illustrated by a broken line in the figures.

This arrangement aligns the respective receiving device 11 or 12 centrically to the rotational axis 10 in the measuring position, and this makes the operation by a doctor particularly intuitive.

FIG. 2A shows the support 5 in a position suitable for producing an analog (x-ray film) image of the female breast 7 using the x-ray film in an exchangeable receiving device 11, and the control device 15.

FIG. 2B shows the support 5 in a center pivot position.

FIG. 2C shows the support 5 in a position in which the low resolution digital sensor 12 is located in a measuring position in such a way that it is possible to create a digital (FFDM) image of the female breast 7.

FIG. 3 shows an alternative example of an arrangement of a support for receiving devices of the medical imaging equipment 1, shown in FIGS. 1A and 1B. FIG. 3 is a schematic sectional view perpendicular to the rotational axis 10.

The support for the receiving devices shown in FIG. 3 differs from the first example in that the support 5' carries a CCD sensor 17 for creating high-resolution detailed recordings of the female breast 7, in addition to the low-resolution digital sensor 12 for generating FFDM images, and the scattered radiation grid 14. The receiving surface of the high-resolution CCD sensor 17 using commercially available technology is smaller than that of the low-resolution digital sensor 12.

If necessary, an antiscatter grid can also be provided in front of the CCD sensor.

A shield 18, which may be a lead plate, is provided between the high-resolution CCD sensor 17 and the low-resolution digital sensor 12, the shield also being carried by the support 5'. The shield 18 shields the respective receiving surface 17 or 12 not located in the measuring position from the beam path of the x-rays 4 and in this way prevents x-rays 4 from being able to emerge on the underside of the support 5'. In this way, a patient's exposure to radiation is reduced. Moreover, it prevents the receiving surface 17 or 12 not located in the measuring position being exposed unintentionally and also prevents this receiving surface 17 or 12 being exposed to radiation.

As an alternative to using lead for the shield 18, when very soft x-rays (approximately 20-35 kV) are used, another material that is opaque to soft x-rays may be used. This is beneficial in terms of environmental protection. Soft x-rays may be used in mammography.

The rotational axis 10 is not arranged within the support 5' between the two receiving surfaces 12 and 17, but outside the support 5'. Thus in order to pivot the support 5' about the rotational axis 10, provision is made for the use of a second bracket 19. The receiving surfaces 12 and 17 may not be bisected by a respective perpendicular projection of the rotational axis 10.

A construction of this kind is practical when the mechanics required for the rotational axis 10 cannot be provided within the support for reasons, for example, of space.

Pivoting the support 5' results in a relatively wide movement, and the two receiving devices 12 and 17 in the respective measuring position are not located in the same place but in both horizontally and vertically displaced places.

This may result in horizontal or vertical compensating devices (not shown in the figures) having to be provided in order to arrange the respective receiving device in focus in the beam path of the x-rays.

FIG. 4 shows a second example of the support 5" of a receiving device of medical imaging equipment 1. FIG. 4 is also a cross-sectional view through the support 5" parallel to the rotational axis 10.

The support 5" carries a mounting for holding an exchangeable x-ray film 11', a large-surface low-resolution digital sensor 12 for creating FFDM images, as well as a high-resolution CCD sensor 17' for creating detailed recordings of the female breast 7. A scattered radiation grid 14 is provided above the low-resolution digital sensor 12.

A suitably adapted filter (not shown) may also be provided above the aperture for the exchangeable x-ray film 11' and/or above the high-resolution CCD sensor 17'.

The receiving devices 11', 12 and 17' have surfaces parallel to the rotational axis 10. A perpendicular projection 16, 16', 16" of the rotational axis 10 on the receiving device surfaces 11', 12 and 17' bisects the receiving device 11' and 12. However, in the example shown, the receiving device 17' is not bisected.

An arrangement where a perpendicular projection 16" of the rotational axis 10 does not bisect the receiving device 17' may be useful as when, with the receiving device 17' in measuring position, the object for measurement 7 should not or cannot be arranged centrally above the rotational axis 10.

The support 5" is configured so the receiving devices 11', 12 and 17', which it carries, are disposed in such a way that adjacent receiving devices are disposed at an angle β of essentially 60° with respect to each other.

To enable the support 5" to pivot with the minimum width of movement possible, the rotational axis 10 in the example shown in FIG. 4 is disposed at the geometric center of the volume encompassed by the support 5" for the receiving devices 11', 12 and 17'.

Even though the arrow depicted in FIG. 4 indicates the support 5" pivoting in an anticlockwise direction about the rotational axis 10, the support 5" may also be pivoted about the rotational axis 10 as desired in a clockwise direction or, alternately, in a clockwise and in an anticlockwise direction.

Figure 5:
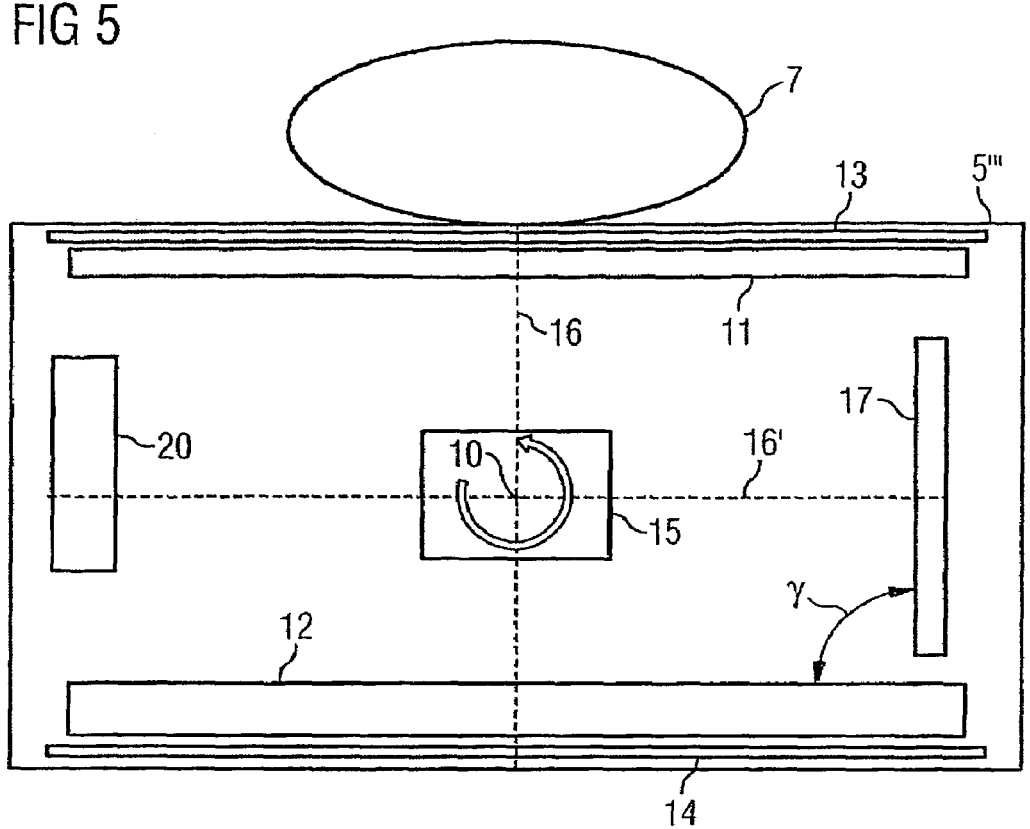
FIG. 5 shows a schematic sectional view through a support and receiving devices of a third example.
Figure 6:
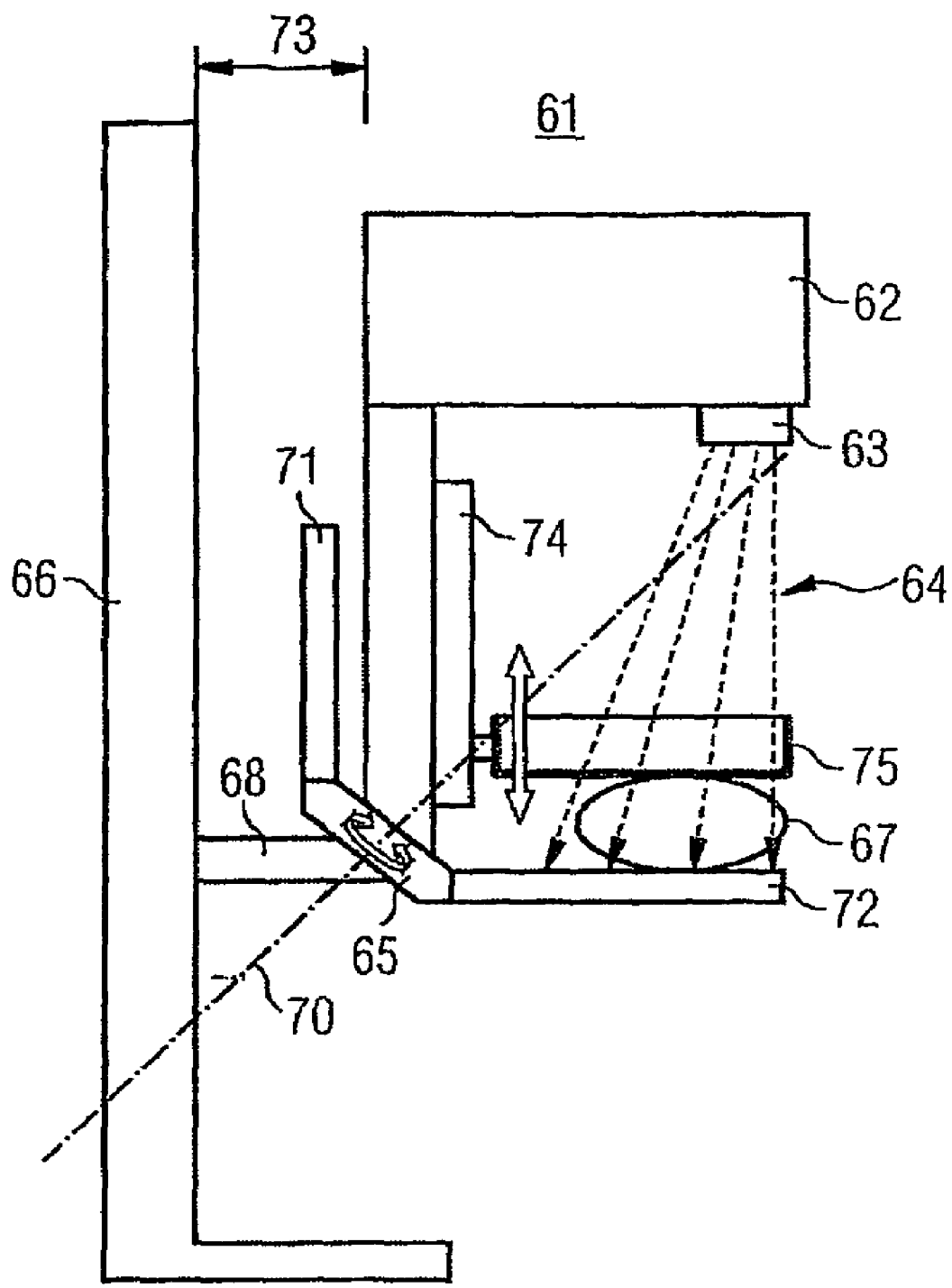
FIG. 6 shows a schematic representation of medical imaging equipment for obtaining mammographic images according to the prior art.

FIG. 5 shows a third example of a support 5''' of the receiving devices of the medical imaging equipment 1 according. FIG. 5 is also a schematic cross-sectional view through the support 5''' parallel to the rotational axis 10.

The support 5''' carries an exchangeable removable x-ray film cassette 11, a large-surface low-resolution digital sensor 12 for creating FFDM images, a high-definition CCD sensor 17 for creating detailed recordings of the female breast 7 and a luminescence radiography screen 20. Scattered radiation grids 13 or 14 are arranged respectively in front of the exchangeable x-ray film cassette 11 and the low-resolution digital sensor 12.

A suitably adapted scattered radiation grid may also be provided above the small-surface high-resolution CCD sensor 17 and also above the luminescence radiography screen 20.

The pivot axis is arranged in the geometric center of the volume encompassed by the support 5''' for the receiving devices 11, 12, 17 and 20. Thereby, the receiving devices 11, 12 and 17 are arranged in such a way that the perpendicular projections 16 or 16' onto the respective receiving surfaces bisect said receiving surfaces. Adjacent receiving devices 11, 12, 17, 20 make an angle γ of substantially 90° with respect to each other.

The support 5''' shown in FIG. 5 and may be a compact design and create mammographic images using four different measuring methods and hence to adapt the measuring method to the respective application in an optimal manner.

In the previous examples, the use of x-ray films, low-resolution digital sensors/detectors for FFDM images, high-resolution CCD sensors for detailed recordings as well as the luminescence radiography screen as a receiving device were disclosed, it is obvious that the receiving devices can be realized by alternative measuring devices having a sensitivity to the measuring radiation that now exist or may be developed. Further, the support for the receiving devices can also carry more than four receiving devices.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. A medical imaging equipment, comprising:
   a radiation source;
   at least two receiving devices;
   a measuring region disposed in a beam path between the radiation source and the receiving devices, in which an object for measurement is disposable; and
   a support mounted to the medical imaging equipment and pivotable about a rotational axis that is substantially perpendicular to the beam path, the support adapted to mount the at least two receiving devices;
   wherein at least two of the receiving devices have differing spatial resolution;
   wherein, the support is operable to alternatively rotate the at least two receiving devices into a measuring position.

2. The medical imaging equipment as in claim 1, wherein the rotational axis makes an angle ($\alpha$) of between about 80° and about 100° with respect to the beam path.

3. The medical imaging equipment as in claim 2, wherein the angle ($\alpha$) is between 85° and 95°.

4. The medical imaging equipment as in claim 3, wherein the angle ($\alpha$) is between 88° and 92°.

5. The medical imaging equipment as in claim 1, wherein the rotational axis is disposed between the receiving devices.

6. The medical imaging equipment as in claim 5, wherein the surface of each receiving device is bisected by a perpendicular projection of the rotational axis.

7. The medical imaging equipment as in claim 5, wherein the rotational axis is arranged centrally in the beam path.

8. The medical imaging equipment as in claim 7, the rotational axis is arranged in the geometric center of a volume of the support.

9. The medical imaging equipment as in claim 8, wherein the support further comprises a shield disposed in the beam path for receiving devices that are not located in the measuring position.

10. The medical imaging equipment as in claim 1, wherein the rotational axis is arranged centrally in the beam path.

11. The medical imaging equipment as in claim 1, the rotational axis is arranged in the geometric center of a volume of the support.

12. The medical imaging equipment as in claim 1, wherein the support has a contact surface for the object for measurement.

13. The medical imaging equipment as in claim 1, wherein a dosage measuring device is mounted to the support and disposed between at least two receiving devices.

14. The medical imaging equipment as in claim 1, wherein the support further comprises a shield disposed in the beam path for receiving devices that are not located in the measuring position.

15. The medical imaging equipment as in claim 1, wherein surfaces of two of the receiving devices are parallel to each other.

16. The medical imaging equipment as in claim 1, wherein the support is adapted to mount three receiving devices, and surfaces of adjacent receiving devices are disposed at an angle ($\beta$) of substantially 60° with respect to each other.

17. The medical imaging equipment as claimed in claim 1, wherein the support is adapted to mount four receiving devices, and surfaces of adjacent receiving devices are disposed at an angle ($\Upsilon$) of substantially 90° with respect to each other.

18. The medical imaging equipment as in claim 1, wherein at least one of the receiving devices is a solid state detector for x-rays.

19. The medical imaging equipment as in claim 1, wherein the at least one of the receiving devices is a charge-coupled-device (CCD) sensor.

20. The medical imaging equipment as in claim 1, wherein at least one of the receiving devices is a cassette for x-ray film.

21. The medical imaging equipment as in claim 1, wherein at least one of the receiving devices is a luminescence radiography screen.

22. The medical imaging equipment as in claim 1, wherein the medical imaging equipment is configurable to obtain mammographic images.

23. A medical imaging equipment, comprising:
   a radiation source;
   a first receiving device and a second receiving device;
   a support adapted to mount the first and second receiving devices and pivotable about a rotational axis that is substantially perpendicular to a beam path between the radiation source and the support,
   wherein the first receiving device is disposed in a measuring position that is exposed to a radiation beam from the radiation source, and the second receiving device being disposed in a non-measuring position that is not exposed to the radiation beam from the radiation source, and
   wherein the support is operable to rotate the second receiving device into the measuring position and the first receiving device into the non-measuring position, and the first and second receiving devices have differing spatial resolutions.

* * * * *